United States Patent [19]

Trost et al.

[11] Patent Number: 5,446,225

[45] Date of Patent: * Aug. 29, 1995

[54] PALLADIUM CATALYZED AKYLATIVE CYCLIZATION USEFUL IN SYNTHESES OF VITAMIN D AND ANALOGUES

[75] Inventors: Barry M. Trost, Los Altos Hills, Calif.; Jacques Dumas, Cologne, Germany

[73] Assignee: Board of Trustees of the Leland Stanford Junior Univ., Stanford, Calif.

[ * ] Notice: The portion of the term of this patent subsequent to Mar. 8, 2011 has been disclaimed.

[21] Appl. No.: 173,172

[22] Filed: Dec. 23, 1993

Related U.S. Application Data

[63] Continuation-in-part of Ser. No. 49,607, Apr. 20, 1993, Pat. No. 5,292,977, which is a continuation of Ser. No. 831,687, Feb. 5, 1992, abandoned.

[51] Int. Cl.$^6$ ............... C07C 13/36; C07C 13/38; C07C 403/00
[52] U.S. Cl. ................. 585/359; 585/360; 585/366; 570/187; 570/214
[58] Field of Search ............ 585/359, 360, 366, 367, 585/612; 570/187, 214

[56] References Cited

U.S. PATENT DOCUMENTS 5,292,977  3/1994  Trost et al. ............... 585/359

OTHER PUBLICATIONS

Huebel et al., "In–vivo Effect of 1,25–dihydroxy Vitamin D3 on Phagocyte Function in Hemodialysis Patients," *Kidney International*, 40 (5), (1991), pp. 927–933.

Arnold et al., "Induction of Epidermal Ornithine Decarboxylase Following Tape Stripping is Inhibited by a Topical Vitamin D3 Analogue MC–903," *British Journal of Dermatology*, 125 (1), (1991), pp. 6–8.

Binderup et al., "20–Epi–Vitamin D3 Analogues: A Novel Class of Potent Regulators of Cell Growth and Immune Responses," *Biochemical Pharmacology*, 42 (8), (1991) pp. 1569–1575.

Barton et al., in their 1973 description of the synthesis of
. (List continued on next page.)

*Primary Examiner*—Asok Pal
*Attorney, Agent, or Firm*—Majestic, Parsons, Siebert & Hsue

[57] ABSTRACT

An alkylative cycloaddition method is provided that is particularly useful for the synthesis of many of the Vitamin D analogues with differing side chains. Thus, a preferred synthesis is of Vitamin D analogues having a side chain $R_1$ where a first precursor having the structure

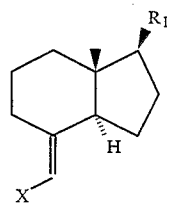

with X being a halide or a pseudo halide, and a second precursor are provided, the second precursor being a 1,7 enyne. These precursors are reacted in the presence of a palladium catalyst to form compounds having the structure

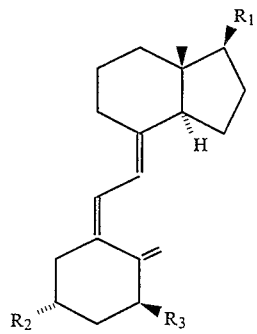

where $R_2$ is hydrogen, hydroxyl, lower alkoxy, fluorine, or a protecting group, and $R_3$ is hydrogen, hydroxyl, lower alkoxy, fluorine, or a protecting group.

13 Claims, No Drawings

OTHER PUBLICATIONS

1α-hydroxy-Vitamin $D_3$, *Journal of the American Chemical Society*, 95 (8), (Apr. 18, 1973) pp. 2748–2749.

Posner et al., "Asymmetric Total Synthesis of an A-Ring Precursor to Hormonally Active 1α,25-Dihydroxyvitamin $D_3$", *The Journal of Organic Chemistry*, 55 (13), Jun. 22, 1990), pp. 3967–3969.

Chodynski et al., "Synthesis of Side-Chain Homologated Analogs of 1,25-Dihydroxycholecalciferol and 1,25-Dihydroxyergocalciferol," *Steroids*, 56, (Jun. 1991), pp. 311–314.

Gill et al., "The Synthesis and Biological Activity of 22-Fluorovitamin $D_3$: A New Vitamin D Analog," *Steroids*, 48 (1–2), (Jul.–Aug. 1986), pp. 93–108.

Gill et al., "Synthesis and Biological Activity of Novel Vitamin D Analogues", *Journal of Medical Chemistry*, 33 (1990), pp. 480–490.

Onisks et al., "25-Azavitamin $D_3$, an Inhibitor of Vitamin D Metabolism and Action", *Journal of Biological Chemistry*, 254:9 (May 10, 1979), pp. 3493–3496.

Sai et al., *Chem. Pharm. Bull.*, 33, (1985), pp. 878–881.

Tanaka et al., "25-Hydroxy-26,26,26,27,27,27-Hexafluorovitamin $D_3$: Biological Activity in the Rat", *Arch of Biochem & Biophys*, 218 (1), (Oct. 1, 1982), pp. 134–141.

Corradino et al., "Induction of Calcium-Binding Protein in Organ-Cultured Chick Intestine by Fluoro Analogs of Vitamin $D_3$", *Arch of Biochem & Biophys*, 208 (1), (Apr. 15, 1981), pp. 273–277.

Esvelt et al., "Calcitroic Acid: Biological Activity and Tissue Distribution Studies", *Arch. of Biochem & Biophys*, 206 (2), (Feb. 1981), pp. 403–413.

Holick et al., "Relationship of 25-Hydroxyvitamine $D_3$ Side Chain Structure to Biological Activity," *J. of Biol. Chem.*, 250 (1), (Jan. 10, 1975), pp. 226–230.

Ostrem et al., "The Vitamin D-Induced Differentiation of HL-60 Cells: Structural Requirements", *Steroids*, 49 (1/3), (Jan.–Mar. 1987), pp. 73–102.

PALLADIUM CATALYZED AKYLATIVE CYCLIZATION USEFUL IN SYNTHESES OF VITAMIN D AND ANALOGUES

This invention was made with Government support under contract GM13598 awarded by the National Institutes of Health. The Government has certain rights in this invention.

This is a continuation-in-part of Ser. No. 08/049,607, filed Apr. 20, 1993, now U.S. Pat. No. 5,292,977, issued Mar. 8, 1994, which was a continuation of Ser. No. 07/831,687, filed Feb. 5, 1992, now abandoned.

FIELD OF THE INVENTION

This invention generally relates to use of enynes in palladium catalyzed alkylative cyclizations, and more particularly where a 1,6-enyne or 1,7-enyne is reacted with an aryl halide or pseudo halide, a vinyl halide or pseudo halide, or an alkyl halide or pseudo halide lacking a β-hydrogen in the presence of a palladium catalyst to generate 1,2-bis-alkylidenecycloalkanes, such as Vitamin D analogues.

BACKGROUND OF THE INVENTION

As is well known, Vitamin $D_2$ (also known as "calciferol") and Vitamin $D_3$ (also known as "cholecalciferol") are effective in humans as antirachitic nutritional factors. Vitamin $D_2$ is obtainable from ergosterol by uv irradiation in a suitable solvent, and Vitamin $D_3$ can be obtained by irradiation of its provitamin, 7-dehydrocholesterol. In about the early 1970s, interest developed in 1α,25-dihydroxycholecalciferol, which is the polar, biologically active, metabolite of Vitamin $D_3$, due to an extremely rapid onset of physiological activity. A few years later, another new Vitamin $D_3$ analogue, again with rapid onset of physiological activity, was described by Barton et al (1α-hydroxy-Vitamin $D_3$).

Several of these Vitamin D analogues are illustrated by reference to the Formula 1 structure. In the case of 1α,25-dihydroxycholecalciferol, Y is hydroxyl as are both $R_2$ and $R_3$. For 1α-hydroxy-Vitamin $D_3$, Y is hydrogen while both $R_2$ and $R_3$ are hydroxyl.

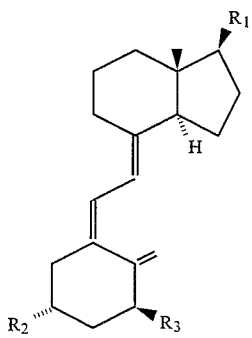

FORMULA 1

The Formula 1 structure can be further generalized (and often is, particularly in description of syntheses) by more generally representing the side chain of which $R_1$ of the Formula 1 representation is a part.

Vitamin D analogue syntheses have received considerable attention, particularly recently, due to evidence that various Vitamin $D_3$ related compounds are hormonally active and may be clinically useful regulators of various fundamental physiological processes. Thus, for example, 1,25-dihydroxy-Vitamin $D_3$ has been shown to modulate the immune function of monocytes and macrophages, Huebel et al., "In-vivo Effect of 1,25-dihydroxy Vitamin $D_3$ on Phagocyte Function in Hemodialysis Patients," *Kidney International*, 40 (5), pp. 927–933 (1991). Calcipotriol (also known as "MC-903") is an analogue of the physiologically active metabolite of Vitamin $D_3$, 1α, 25-dihydoxycholecalciferol, which is indicated as efficacious in reducing in hyperproliferation for psoriasis patients by Arnold et al., "Induction of Epidermal Ornithine Decarboxylase Following Tape Stripping is Inhibited by a Topical Vitamin $D_3$ Analogue MC-903," *British Journal of Dermatology*, 125 (1), pp. 6–8 (1991). Binderup et al., "20-Epi-Vitamin $D_3$ Analogues, A Novel Class of Potent Regulators of Cell Growth and Immune Responses," *Biochemical Pharmacology*, 42 (8), pp. 1569–1576 (1991), found the 20-Epi-Vitamin $D_3$ analogues (structurally related to 1α,25-dihydroxycholecalciferol) to be very potent inhibitors of T-lymphocyte proliferation induced by interleukin-1 or alloantigen. These 20-epi-Vitamin $D_3$ analogues are characterized by an altered stereo-chemistry at carbon 20 of the side chain.

Thus, various Vitamin D analogues are of potential interest in therapeutic applications, such as in the prevention of graft rejections and in the treatment of cancer and auto-immune diseases, as well as in the treatment of psoriasis.

These increasingly interesting potential clinical applications of Vitamin D analogues have enhanced interest in simplifying their syntheses. Two strategies for 1α-hydroxy-Vitamin D analogues are currently employed. One is based on a biomimetic path from a normal steroid precursor, such as, for example, reported by Barton et al. in their 1973 description of the synthesis of 1α-hydroxy-Vitamin $D_3$, *J. Am. Chem. Soc.*, 95 (8), pp. 2748–2749 (1973). The other current strategy is based on a convergent approach of attaching a preformed ring A system to a CD fragment (Grundmann ketone or an analogue thereof), such as is illustrated by Posner et al., *J. Org. Chem.*, 55, pp. 3967–3969 (1990).

Accordingly, a simple convergent strategy that can readily be adopted for the synthesis of many Vitamin D analogues, particularly those with differing side chains, would be useful to prepare compounds that are presently clinically useful, as well as analogues for potential clinical uses in this rapidly developing field.

SUMMARY OF THE INVENTION

In one aspect of the present invention, an alkylative cycloaddition method is provided permitting the formation of substituted bis(alkylidene)cycloalkanes as reaction products in which a 1,6 enyne or a 1,7-enyne is reacted with a selected compound RX where "X" is a halide or pseudo halide (a substituent that functions in the given reaction in a fashion similar to that of a halide). The alkylative cycloaddition is performed in the presence of a palladium catalyst and is characterized by remarkable diastereoselectivity. One application of this alkylative cycloaddition method is wherein the selected compound RX is a derivative of Grundmann's ketone. Thus, RX having the structure

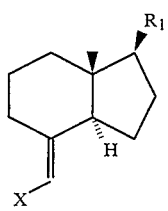

(where $R_1$ is to be a Vitamin D analogue side chain and X is a halide or pseudo halide) is useful as a Vitamin D analogue by reaction with a 1,7 enyne (and with the generation of a new carbon-carbon bond to cyclize the enyne).

A particularly preferred embodiment for application of the alkylative cycloaddition method is in the convergent synthesis of Vitamin D analogues with a side chain $R_1$, such as by forming reaction products having the structure

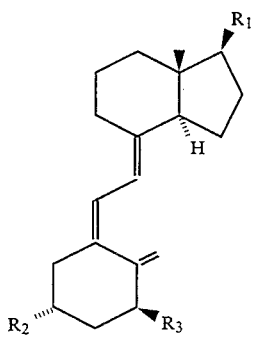

where $R_1$ is the Vitamin D analogue side chain, $R_2$ is hydrogen, fluorine, hydroxyl, lower alkoxy, or a removable protecting group, and $R_3$ is hydrogen, fluorine, hydroxyl, lower alkoxy, or a removable protecting group.

DETAILED DESCRIPTION OF THE PREFERRED EMBODIMENTS

Substituted 1,2-bis(alkylidene)cycloalkanes are valuable building blocks in chemical syntheses as well as interesting substances in their own right. Broadly, an alkylative cycloaddition of this invention provides entry to substituted bis-alkylidenecycloalkanes possessing Z stereospecificity as is designated by Reaction (1), which is illustrated by Ser. No. 08/049,607, incorporated herein by reference.

Briefly, Reaction (1) is wherein a 1,6 or 1,7 enyne (sometimes designated as "pre A") is reacted with a compound RX (sometimes hereinafter referred to as "pre CD" for the application to Vitamin D analogues) in the presence of a palladium catalyst to form a substituted bis(alkylidene)cycloalkane as reaction product in an alkylative cycloaddition. (Where R of RX is vinyl, then a cyclohexadiene can be obtained after thermal cyclization.) The "X" of RX is a halide (preferably bromide or iodide) or a pseudo halide, and "R" is a vinyl, an aryl, or an alkyl lacking a β-hydrogen. This new method for ring construction permits an extremely wide selection of available choices for the R moiety and permits introduction of both electron donating and withdrawing substituents on the terminal olefinic carbon of the enyne in order to prepare bis-alkylidenecycloalkanes with five and six membered rings.

By "pseudo halide" suitable for "X" of the "RX" compound is meant a moiety (atom or substituent), which when bound to carbon has been shown to have the ability to undergo an oxidative addition to Pd(0) complexes to generate a carbon-palladium bond for further C—C bond forming reactions catalytic in palladium. Some illustrative pseudo halides useful in practicing this invention are: trifluoromethanesulfonate (triflate), more generally represented as $ROSO_2CR_3$ and exemplified by Scott et al., *J. Org. Chem.*, 50 (1985), 2302, and, Scott and Stille, *J. Am. Chem. Soc.*, 108 (1986), 3033; polyfluoroalkanesulfonates; fluorosulfonates, especially fluorosulfonate esters such as exemplified by Chen and He, *Synthesis*, (1988), 896, and Lu and Zhu, *Synthesis*, (1986), 726; dialkylphosphates, such as represented as $ROP(O)(OR')_2$ and exemplified by Fugami et al., *Chem. Lett.*, (1987), 2203; diazonium salts, generally represented as $RN_2{}^+X^-$ and exemplified by Sengupta and Bhattacharya, *J. Chem. Soc.* Perkins I, (1993), 1943; and sulfonyl chlorides, generally represented by $RSO_2Cl$ and exemplified by Mivra et al., *Tetrahedron Lett.*, 30 (1989), 975.

The use of a pseudo halide rather than a halide for the "RX" compound tends to result in reduced yields; however, by providing a source of halide ions, preferably iodide, bromide, or chloride, in the reaction mixture then yield is increased to acceptable levels. The amount of halide ions provided may be small (such as a catalytic amount), but preferably is in a slight molar excess with respect to the amount of pseudo halide. Illustrative sources of halide ions when one practices the invention with pseudo halides include tetraalkylammonium halides such as tetra-n-butylammonium bromide, tetraalkylphosphonium halide such as tetraphenylphosphonium bromide, and metal halides such as lithium bromide. These halide sources are soluble in the organic solvents (such as toluene, benzene, dichloroethane, THF, DMF) in which the inventive reaction is conducted.

There are various alternatives to the reaction conditions in performing the Reaction (1) synthesis. In one method, we have reacted pre A and pre CD in the presence of two mole percent $Pd(OAc)_2$, four mole percent $Ph_3P(TPP)$ and one eq. of silver carbonate (as base). Heating eventually to 75° C. leads to the desired alkylated cycloadduct. In another alternative, we have changed the catalyst to two mole percent $(dba)_3Pd_2.CHCl_3$ and four mole percent tri-o-tolylphosphine (TOT). We have also replaced silver carbonate with triethylamine. In a third variation, we have used five mole percent $Pd(OAc)_2$, fifteen mole percent (TPP) and varying amounts of triethylamine (such as from 1 eq. to a 1:1 mixture with the solvent) in refluxing toluene.

We have demonstrated utility of pseudo halides, with the preferred inclusion of halide ions, by means of a model reaction in which the RX compound used to illustrate pseudo halide suitability was vinyl triflate (trifluoromethanesulfonate). A number of different halide sources have been used (LiBr, Bu4NBr, Bu4NCl, Bu4NI, Oc4NBr). Other variations have been the use of various ligands (e.g. P(o-anisyl)3, P(o-tolyl)3, P(2-furyl)3, AsPh3) and a temperature range preferably on the order of about 75° C. to about 100° C. Table 2 of Example 9 illustrates a number of the reaction condition variations used with the model pseudo halide alkylative cyclization.

Accordingly, various reaction conditions can be used to accomplish the reaction (1) alkylative cycloaddition whether one uses "X" of RX as halide or as pseudo halide, although the palladium catalyst should be a palladium zero complex in its active state, and at least some of the ligands should be trivalent phosphorous compounds, such as phosphines or phosphites.

Some of the different enynes and some of the different RX compounds in which we have demonstrated successful alkylative cyclizations are summarized by Table 1 of incorporated Ser. No. 08/049,607.

Our particularly preferred mode of carrying out this invention is as a new convergent strategy in which ring A of Vitamin D analogues is created from the pre A, acyclic unit as a result of attaching this unit to a Grundmann's ketone derivative (as pre CD) while utilizing a Pd catalyzed alkylative enyne cyclization, as illustrated in Reaction (2).

REACTION (2)

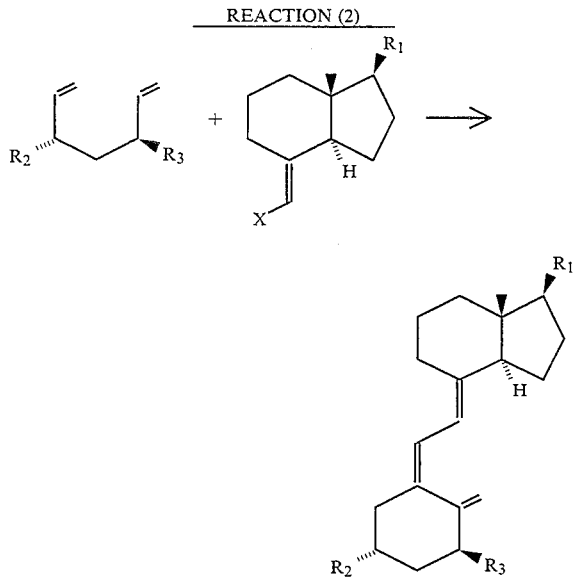

(wherein $R_1$ is a Vitamin D analogue side chain, $R_2$ is hydroxyl, lower alkoxy, fluorine, or a removable protecting group, $R_3$ is hydrogen, hydroxyl, lower alkoxy, fluorine, or a removable protecting group), and X is halide or pseudo halide.

The enyne used can be substituted or unsubstituted. For example, the saturated carbons of the enyne can be substituted with heteroatom substituents such as halogen, oxygen (ethers, silyl ethers, etc.), and nitrogen (such as dialkylamino). Thus, use of the term "1,6 or 1,7 enyne" is broadly meant to include substituted enynes. Further, considerable variety in the $R_1$ moiety is possible (which means that analogues of Grundmann's ketone varying in the side chain can correspondingly tolerate quite a broad range of side chains). A number of literature articles have illustrated such side chain variations, which are intended to be included within the scope of the subject invention. For example, the following articles have described some of the various such side chains, the disclosures of which are incorporated herein by reference: Chodynski and Kutner, *Steroids*, 56, 311 (1991); Gill et al., *Steroids*, 48, 93 (1986); Gill et al., *J. Med. Chem.*, 33, 480 (1990); Onisks et al., *J. Biol. Chem.*, 254, 3493 (1979); Sai et al., *Chem. Pharm. Bull.*, 33, 378 (1985); Tamaka et al., *Arch. Biochem. Biophys.*, 218, 314 (1982); Corradins et al., *Arch Biochem. Biophys.*, 208,273 (1981); Esvelt and De Luca, *Arch Biochem. Biophys.*, 206, 403 (1981); Holick et al., *J. Biol. Chem.*, 250,226 (1975); and Ostrem and De Luca, *Steroids*, 49, 73 (1987).

The simple convergent strategy illustrated by Reaction (2) can readily be adopted for the synthesis of many of the hydroxylated Vitamin D analogues which differ in the side chain through Grundmann's ketone analogues. The ability to use a simple acyclic unit such as pre A as the precursor for the A ring also facilitates variations of substituents on the A ring.

The following examples are intended to illustrate, but not limit, the scope of this invention. Example 1 outlines asymmetric synthesis of a suitable pre A for preparing a Vitamin D analogue.

EXAMPLE 1

At −78° C., ozone in oxygen is bubbled into a solution of 1,1-diethoxy-but-3-ene (2.88 g, 20mmol.) in dichloromethane (40 mL) until a blue color persists. The flask is then purged with oxygen for 30 minutes. To this cold solution is added triphenylphosphine (5.25 g, slight excess) in one portion, and the cold bath is removed. After 2 hours stirring at room temperature, the solution is dried (MgSO$_4$) and concentrated. The triphenylphosphine oxide present in the oily residue is crystallized by successive addition of pentane (20 mL) and ethyl ether (50 mL), and removed by filtration. The resulting pentane/ethyl ether solution of 3,3-diethoxypropanal is redried (MgSO$_4$), and dropwise added to a propargyl Grignard solution (prepared from 40 mmol. propargyl bromide and 50 mmol. magnesium in 50 mL ethyl ether) at 0° C. The reaction is instantaneous. After 15 minutes stirring at room temperature, water (5 mL) is slowly added. After decantation and extraction of the wet salts with ethyl ether (2×20 mL), the combined organic phases are dried (MgSO$_4$), concentrated, and distilled (Kugelrohr) to afford 2.71 g of 1,1-diethoxy-hex-5-yne-3-ol as an oil (73% from 1,1-diethoxy-but-3-ene, bp=140°–145° C./0.1 mmHg).

IR (neat): 3450, 3298, 2977, 2931, 1376, 1346 cm$^{-1}$. $^1$H NMR (200 MHz): 1.21 (t, 6H, J=7Hz), 1.82 and 1.95 (complex AB, 2H), 2.06 (t, 1H, J=2.5Hz), 2.33 and 2.43 (complex B, 2H), 3.45–3.80 (m, 4H), 3.95 (m, 1H), 4.72 (t, 1H, J=6.5Hz). $^{13}$C NMR: 14.8, 14.9, 26.7, 38.9, 61.2, 62.0, 66.6, 70.3, 80.6, 101.6.

To the above material (1.86 g, 10 mmol) in dry DMF (10 mL) are successively added imidazole (2.1 g, 3 eq.) and tert-butylchlorodiphenyl silane (4.12 g, 1.5 eq.). The resulting pale brown solution is heated at 65° C. for 18 hours then cooled down, and poured into a suspension of water (30 mL) and pentane (100 mL). The organic phase is separated, and the aqueous phase extracted with pentane (2×20 mL). The combined organic phases are washed with water (10 mL), dried (MgSO$_4$), and concentrated. Chromatography of the oily residue (ethyl ether/hexanes, 1/5) affords the tert-butyldiphenylsilyl ether (3.52 g, 83%) as a colorless oil.

IR (neat): 3311, 2973, 2932, 2859, 1473, 1428, 1377 cm$^{-1}$. $^1$H NMR (200 MHz): 1.06 (s, 9H), 1.08 (t, 3H, J=7Hz), 1.12 (t, 3H, J=7Hz), 1.86–2.08 (m, 3H), 2.23 and 2.34 (complex AB, 2H), 3.17–3.62 (m, 4H), 4.00 (m, 1H), 4.68 (bt, 1H, J=6.5Hz), 7.30–7.50 and 7.65–7.75 (2m, 10H). $^{13}$C NMR: 15.0, 15.1, 19.1, 26.8, 27.0, 60.3, 61.0, 68.3, 70.4, 80.9, 100.1, 127.7, 127.8, 129.8, 133.8, 134.2, 136.1. Anal. Calc'd for C$_{26}$H$_{36}$O$_3$Si: C,73.54%; H,8.54%. Found: C, 73.75%; H, 8.74%.

To a stirred suspension of the just described ketal (0.51 g, 1.2 retool) in THF (5 mL) and water (1 mL) is added trifluoroacetic acid (2 mL). The reaction mixture becomes homogeneous. After 1.5 hours stirring at room temperature, the reaction mixture is poured into a suspension of potassium carbonate (5 g), water (20 mL), and ethyl ether (50 mL). After decantation, the aqueous phase is extracted with ethyl ether (2×30 mL), and the combined organic phases are washed with 10% aqueous NaCl, dried (MgSO$_4$), and concentrated to afford 0.41 g of material (98/2 mixture of 3-tert-butyldiphenyl silyloxy-hex-5-yne-1-al and the ketal by GC analysis), which is immediately dissolved in dry THF (7 mL), and cooled to −78° C. To this solution is dropwise added vinyl magnesium bromide (1M solution in THF, 3 mL) and the resulting suspension stirred for 30 minutes at −78° C. Water (1 mL) is then slowly added, then the temperature raised to room temperature. The organic phase is separated by decantation, and the moist inorganic salts are extracted with ethyl ether (2×20 mL). The combined organic phases are dried (MgSO$_4$) and concentrated. Chromatography of the oily residue (ethyl ether/pentane 1/3) affords the product of Formula 2 structure:

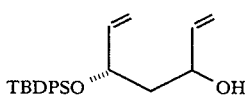

FORMULA 2

The Formula 2 product was obtained as 0.355 g of diastereoisomeric mixtures designated "2a" and "2b" (ca. 1.5:1). Total yield was 78%. 1.79 g of this mixture is separated by MPLC (hexanes/ethyl ether, 4/1) to afford successively:

590 mg of minor anti isomer (2b)
100 mg of diastereomeric mixture
980 mg of major syn isomer (2a).

The stereoisomeric purity of each isolated isomer is greater than 95% (no peak detected by $^1$H NMR).

IR (neat, mixture): 3410 (broad), 3298, 2912, 2851, 2117, 1585, 1465, 1420 cm$^{-1}$. Data for where 3R*,5R* (that is, mixture 2a) Colorless oil. $^1$H NMR (300 MHz): 1.05 (s, 9H), 1.78–1.95 (m, 3H), 2.28 (complex AB, 2H), 4.03 (bq, 1H, J=7Hz), 4.31 (m, 1H), 5.02 (bd, 1H, J=11 Hz), 5.13 (bd, 1H, J=17Hz), 5.76 (ddd, 1H, J=6, 11, and 17Hz), 7.32–7.47 and 7.65–7.75 (2m, 10H). $^{13}$C NMR: 19.0, 26.7, 26.9, 42.7, 70.4, 70.7 (double peak), 80.7, 114.5, 127.8, 127.9, 130.0, 130.1, 133.3, 133.9, 136.0, 140.8. Anal. Calc'd for C$_{24}$H$_{30}$O$_2$Si: C,76.14%; H,7.99%. Found: C, 76.13%; H, 8.07%. Data for where 3S*,5R* (that is, mixture 2b) Colorless oil. $^1$H NMR (300 MHz): 1.05 (s, 9H), 1.71 (complex AB, 2H), 190 (t, 1H, J=2Hz), 2.33 (complex AB, 2H), 4.11 (m, 1H), 4.36 (m, 1H), 5.03 (bd, 1H, J=11 Hz), 5.18 (bd, 1H, J=17Hz), 5.79 (ddd, 1H, J=6, 11, and 17Hz), 7.32–7.48 and 7.65–7.75 (2m, 10H). $^{13}$C NMR: 19.0, 26.3, 26.8, 42.0, 69.2, 69.6 70.6, 80.5, 114.2, 127.9, 128.0, 130.1, 130.2, 133.3, 133.7, 136.1, 141.1. Anal. Calc'd for C$_{24}$H$_{30}$O$_2$Si: C,76.14%; H,7.99%. Found: C, 76.36%; H, 7.77%.

The relative stereochemistry of the two isomers was established by NMR analysis, as illustrated by Example 2, with kinetic resolution of the racemic allylic alcohol (3S*,5R*) giving virtually quantitative recovery of the desired scalemic alcohol (3S,5R) of 98% ee, with the resolution being illustrated by Example 3.

EXAMPLE 2

To a stirred solution of alcohol (3R., 5R*) (190 mg, 0.5 mmol) in THF (2 mL) is added tetrabutylammoniumfluoride (1M solution in THF, 0.6 mL, 1.2 eq.) at 0° C. After 1.5 hours stirring at this temperature, the reaction mixture is diluted with hexanes (2 mL), and filtered over silica gel (hexanes/ethylacetate, 1/1) to afford 63 mg of pale yellow oil (90%, IR 3300 and 3360 cm$^{-1}$) which is dissolved in 2,2-dimethoxypropane (2 mL). To the resulting solution is added camphorsulfonic acid (10 mg, ca. 0.01 eq. ) and the mixture is stirred overnight at room temperature, then poured into ethyl ether (20 mL), and washed with 5% aqueous NaHCO$_3$. The organic phase is dried (MgSO$_4$), and carefully concentrated to afford 48 mg of acetonide as a colorless volatile oil.

IR (neat): 3312, 2933, 2924, 2855, 1464, 1380 cm$^{-1}$. $^1$H NMR (200 MHz): 1.2–1.4 (m, 1H), 1.40 (s, 3H), 1.45 (s, 3H), 1.71 (dt, 1H, J=2.5 and 13Hz), 1.99 (t, 1H, J=2.5Hz), 2.24 (ddd, 1H, J=2.5, 7.5, and 17Hz), 2.46 (ddd, 1H, J=2.5, 5.5, and 17Hz), 4.00 (dddd, 1H, J=2.5,5.5, 7.5, and 11.5Hz), 4.35 (dddt, 1H, J=1.5, 2.5, 6, and 11.5Hz), 5.12 (dt, 1H, J=1.5 and 11Hz), 5.26 (dt, 1H, J=1.5 and 17Hz), 5.81 (ddd, 1H, J=6, 11, and 17Hz). $^{13}$C NMR: 19.6 (CH$_3$), 26.0, 29.9 (CH$_3$), 35.7, 67.4, 70.1, 70.4, 80.1, 99.0, 112.4, 115.8, 138.6. MS and peak match: m/z=165.0924 (100%, M+-CH$_3$, calculated 165.0915), 105, 83, 79, 66.

EXAMPLE 3

To a stirred suspension of freshly activated molecular sieves (400 mg), racemic allyl alcohol (3S*, 5R*) (1.4 g, 3.7 mmol, azeotropically dried prior to use), and D(+)-dicyclohexyltartrate (unnatural, 1.39 g, 1.2 eq., recrystallized four times) in dichloromethane (30 mL, distilled from calcium hydride prior to use) is added at 20° C. dropwise freshly distilled titanium isopropoxide (1.1 mL, 1 eq.). The reaction mixture is swirled for 30 minutes at this temperature then tert-butylhydroperoxide (3M in isoctane, 0.82 mL, 0.66 eq., dried over sieves prior to use) is added by syringe at −40° C.

The reaction mixture is placed in the freezer (−20° C. without stirring) for 19 days, then poured in an ice cooled suspension of ferrous sulfate heptahydrate (17.5 g), tartaric acid (9 g), water 120 mL), and dichloromethane (100 mL). The organic layer is separated, and the aqueous phase extracted with dichloromethane (3×100 mL). The organic phases are combined, washed with brine, dried, and concentrated.

Chromatography of the residue (pentane/ethyl ether, 2:1, Rf=0.6) affords 642 mg (46%) of optically enriched product (3S, 5R). [α]$_D^{25}$ −19.7 (c 1.25, CH$_2$Cl$_2$). $^1$H NMR analysis of the S(+)-O-methylmandelic ester: Methoxy group (s, 3H); major isomer 3.35 ppm minor isomer 3.32 ppm The integration shows a 100:1 ratio (98% ee).

The scalemic protected enyne illustrated by Formula 3 below and sometimes referred to as "Enyne 5" was prepared as illustrated by Example 4.

EXAMPLE 4

To a stirred solution of the alcohol from Example 1 (3R*, 5R*) (3a, 378 mg, 1 mmol.) and imidazole (210 mg, 3 eq.) in dry DMF (3 mL) is added tert-butyl chlorodimethylsilane (225 mg, 1.5 eq.). The resulting pale brown solution is heated at 55° C. for 3 hours then cooled, and poured into a suspension of water (30 mL) and ethyl ether (50 mL). The organic layer is separated and the aqueous phase extracted with ethyl ether (2×20 mL). The combined organic phases are washed (20 mL of water), dried (MgSO$_4$), and concentrated. The oily residue is chromatographed (hexanes/ethylacetate 20/1) to afford 430 mg of syn 4-O-terbutyldiphenylsilyl-6-O-tert-butyldimethylsilyl-oct- 1-yne-7-ene-4,6-diol. Yield 87–88%.

The same conditions applied on optically enriched allyl alcohol of Example 3 (98% ee, 100 mg, 0.264 mmol.) afforded the scalemic protected enyne anti isomer of syn 4-o-terbutyldiphenylsilyl-6-O-tert-butyldimethylsilyl-oct-1-yne-7-ene-4,6-diol (117 mg, 90%, $[\alpha]_D^{25} -5.3$ (c 1.74, CH$_2$Cl$_2$) IV-3, Formula 3:

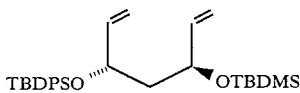

FORMULA 3

Colorless viscous oil.

$^1$H NMR (300 MHz): −0.06 (s, 3H), −0.03 (s, 3H), 0.81 (s, 9H), 1.07 (s, 9H), 1.58-2.06 (m, 3H), 2.31 (complex AB, 2H), 3.94 (bq, 1H, J=5.5Hz), 4.09 (bq, 1H, J=6.5Hz), 4.90-5.06 (m, 2H), 5.63 (ddd, 1H, J=6.5, 11, and 17Hz), 7.32-7.48 and 7.65-7.75 (2m, 10H). $^{13}$C NMR: −5.1, −4.4, 17.9, 19.1, 25.7, 26.8, 27.2, 45.0, 69.1, 70.2, 71.7, 81.2, 114.3, 127.8, 127.7, 129.8, 134.2, 134.4, 136.1, 141.8. Anal. Calc'd for C$_{30}$H$_{44}$O$_2$Si$_2$: C,73.11%; H,9.00%. Found: C,72.91%; H,8.86%. IR (neat): 3313, 3073, 2957, 2931, 2858, 2132, 1590, 1473, 1428 cm$^{-1}$. MS (GC-MS): mz=381, 313, 307, 209, 199, 171.

Grundmann's ketone has the structure illustrated by Formula 4 (where Y=H or OH):

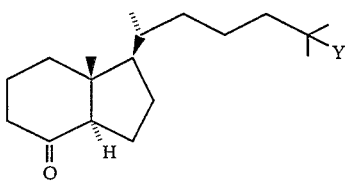

FORMULA 4

Example 5 illustrates a geometrically controlled bromoolefination of Grundmann's ketone.

EXAMPLE 5

To a suspension of bromomethyltriphenylphosphonium salt (545 mg, 5 eq.) in THF (3 mL) is added sodium hexamethyldisilazide (1M in THF, 1.2 mL, 4.8 eq.) at −60° C. The suspension becomes bright yellow after 1 hour. The Grundmann's ketone (Formula 4, Y=H) is added in 0.5 mL of THF, and the cold bath is removed after a few minutes. After 1 hour stirring at room temperature, hexanes (10 mL) are added and the suspension is filtered over a small pad of silica, washing with hexanes. After concentration the oily residue is chromatographed (pentane) to afford the bromide (Formula 5, Y=H) as a colorless viscous oil (53 mg, 62%):

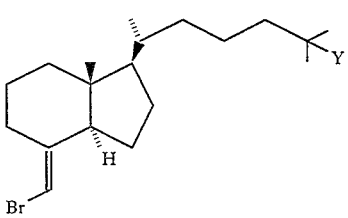

FORMULA 5

E/Z ratio: 30:1 $[\alpha]_d^{25}$ for this mixture: +103, c 1.63, CH$_2$Cl$_2$ IR (neat): 2952, 2869, 1632, 1467 cm$^{-1}$. $^1$H NMR (200 MHz): 0.52 (s, 3H); 0.83 (d, 6H, J=7Hz); 0.90 (d, 3H, J=6Hz); 0.95-2.22 (m, 19H); 2.85 (m, 1H); 5.62 (bs, 1H). $^{13}$C NMR: 11.6, 18.6, 21.8, 22.4, 22.6, 23.6, 27.4, 27.8, 30.9, 35.9 (double peak), 39.3, 39.7, 45.4, 55.8 (double peak), 97.4, 145.5. MS with peak match: m/z=342. 1750 and 340. 1746 (M+, each 1%, calculated 342.1745 and 340. 1765), 229, 227, 207, 147, 105. Anal. Calc'd for C$_{19}$H$_{33}$Br: C, 66.85; H, 9.74. Found: C, 67.00; H, 9.49.

The bromoalkene product obtained from Example 5 is a particularly preferred pre CD in practice of this invention with a particular R$_1$ side chain. However, as earlier discussed, substrates bearing different R$_1$ side chains can readily be utilized in practicing this invention, and rather than bromide another halide or a pseudo halide can be used. Notice in Example 5 the surprisingly high E selectivity in the E/Z ratio of 30:1. Even a 10:1 ratio would typically be considered as "substantially geometrically pure" bromoolefin.

Example 6 illustrates the convergent reaction of the enyne from Example 4 with the bromoolefin of Example 5.

EXAMPLE 6A

Pd$_2$(dba)$_3$CHCl$_3$ (25 mg, 10%) and triphenylphosphine (40 mg, 30%) are mixed under nitrogen in freshly distilled toluene (2.5 mL) and triethylamine (2.5 mL). After 15 minutes, a solution of the Example 4 enyne (156 mg, 0.316 mmol) and the bromide of Example 5 (162 mg, 1.5 eq.) in 0.5 mL fresh toluene is added by gas tight syringe. The resulting yellow solution is vigorously refluxed (120° C.) for 1.5 hours, then cooled and filtered over a small pad of silica gel, washing with pentane. After concentration, the oily residue is chromatographed (pentane/dichloromethane, 10:1) to afford successively:

49 mg of recovered starting bromide 33 mg of "previtamin" among some other impurities.

160 mg of the vitamin having the removable silyl protecting groups.

The "previtamin" fraction is heated under N$_2$ in toluene, at 80° C. for 1 hour, then cooled, and combined with some impure fractions of vitamin. After concentration and flash chromatography (same conditions as above), some 17.5 mg of additional silyated vitamin have been isolated, combined with the first crop, and kept under vacuo for 3 hours to remove any trace of solvent. Total mass of silyated vitamin product was 181 mg (76%).

Data for vitamin product

Colorless viscous oil.

IR (neat): 2952, 2930, 1471, 1428, 1361, 1252 cm$^{-1}$. $^1$H NMR (300 MHz): 0.01 and 0.03 (2s, 6H); 0.51 (s, 3H); 0.80-2.03 (m, 49H); 2.18 (dd, 1H, J=6.5 and 13Hz); 2.30 (bd, 1H, J=13Hz); 2.79 (bd, 1H, J=13Hz); 4.23 (m, 1H); 4.47 (m, 1H); 4.88 (bs, 1H); 5.22 (bs, 1 H); 6.09 (AB, 2H, J=12Hz); 7.30-7.45 and 7.63-7.72 (2m, 10H). $^{13}$C NMR: −5.4, 5.1, 11.7, 18.1, 18.6, 19.0, 22.0, 22.4, 22.6, 23.4, 23.7, 25.7, 26.8, 27.5, 27.8, 28.8, 36.0, 29.3, 40.5, 44.4, 45.0, 45.7, 56.3, 56.6, 68.7, 71.2, 110.5, 117.9, 123.7, 127.7, 127.8, 129.7 (double peak), 134.4, 134.8, 135.1, 136.0, 136.1, 141.3, 149.0.

EXAMPLE 6B (Desilylation of Example 6A product)

To a stirred solution of the silyated vitamin product (181 mg, 0.24 mmol) in THF (1 mL) is added dropwise tetrabutylammonium fluoride (1M in THF, 2 mL, large excess) at room temperature. The solution is stirred for 40 hours then eluted through a small pad of silica gel (ethylacetate). After concentration the oily residue is chromatographed (ethyl acetate) to afford 75 mg of pale yellow solid (79%, mP=131° C. pure by $^1$H NMR). A portion of this material is recrystallized from pentane to afford e-calcidiol as white crystals (mp=133°-134° C.), illustrated by Formula 6, Y=H:

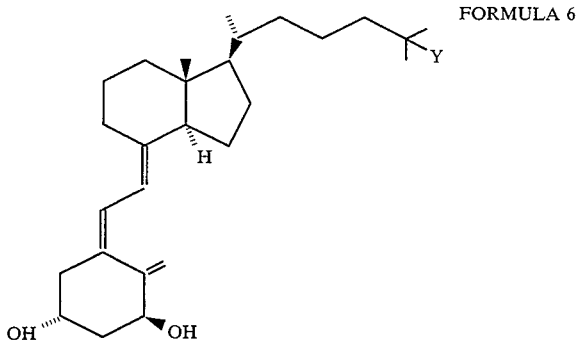

FORMULA 6

$[\alpha]_D^{25}$ +26.5 c 0.89, ethyl ether. IR (neat): 3400 (broad), 2954, 2869, 1645, 1631, 1605, 1467, 1377, 1366, 1054, 959, 909 cm$^{-1}$. UV (ethyl ether): λmax=263 nm, ε=18800. $^1$H NMR (400 MHz): 0.55 (3H, s); 0.98 (6H, 2d, J=6.5Hz); 0.92 (3H, 2d, J=5Hz); 0.95-1.73 (m, 18H); 1.83-2.05 (m, 4H); 2.32 (dd, 1H, J=7 and 13.5Hz); 2.60 (dd, 1H, J=3.5 and 13.5Hz); 2.82 (bd, 1H, J=11.5Hz); 4.23 (m, 1H); 4.43 (m, 1H); 5.01 (bs, 1H); 5.32 (bs, 1H); 6.02 (d, 1H, J=12Hz); 6.39 (d, 1H, J=12Hz). $^{13}$C NMR: 11.8, 18.5, 22.1, 22.4, 22.6, 23.4, 23.7, 27.5, 27.8, 28.9, 36.0, 39.3, 40.3, 42.7, 45.1, 45.8, 56.3, 56.5, 66.8, 70.8, 111.9, 117.0, 125.2, 132.9, 143.6, 147.8. MS with peak match: m/z=400.3342 (5%, M+, calculated 400.3341); 382.3215 (68%, M+-H$_2$O, calculated 382.3236); 364.3103 (77%, M+-2H$_2$O, calculated 364.3130); 349.2880 (M+-2H$_2$O-CH$_3$, calculated 349.2895); 251 (41%); 209 (41%); 195 (48%); 157 (47%); 141 (83%); 131 (50%).

Examples 7 and 8 give an analogous preparation as has just been described but with hydroxyl at the carbon position 25 of this particular R$_1$ side chain to illustrate that side chain variations are readily accommodated in practicing the inventive method.

EXAMPLE 7

To a suspension of bromomethyltriphenylphosphonium bromide (6.54 g, 5 eq.), in dry THF (20 mL) at −78° C. is added sodium hexamethyldisilazide (1M in THF, 15 mL, 5 eq.) by syringe over 5 minutes. Vigorous stirring is continued at this temperature for 1 hour to give a bright yellow slurry. The hydroxylated Grundmann's ketone (Formula 4, X=OH, 840 mg, 3 mmol.) in dry THF (10 mL) is added and the cold bath immediately removed. After about 30 minutes at room temperature, the dark brown reaction mixture is poured into a suspension of ethyl ether (100 mL) and water (30 mL). The aqueous phase is extracted with ethyl ether (2×25 mL). The combined organic phases are washed with water (20 mL), dried (MgSO$_4$), and concentrated to afford 5 g of semisolid material. Careful chromatography (pentane/ethylether, 3:1) affords 490 mg (46%) of bromoolefin of Formula 5, X=OH. $^1$H NMR shows the presence of 2% of Z isomer and 4% of cis fused isomer.

The product is a colorless oil which becomes yellow upon standing at 4° C. for 24 hours, without noticeable change of the NMR spectrum.

$[\alpha]_D^{25}$ +91.4°. (c 2.79, CH$_2$Cl$_2$) IR (neat): 340 (broad), 2962, 1631, 1467 1377 c$^{-1}$. $^1$H NMR (300 MHz): 0.56 (s, 3H), 0.93 (d, 3H, J=6Hz), 0.85-2.05 (m, 24H, including a singlet, 6H, at 1.21 ppm), 2.88 (m, 1H), 5.64 (bs, 1H). $^{13}$C NMR: 11.6, 18.6, 20.6, 21.8, 22.4, 27.4, 29.0, 29.2, 30.9, 35.8, 36.2, 44.2, 45.4, 55.7, 55.8, 71.0, 97.4, 145.4. Anal. Calc'd for C$_{19}$H$_{33}$BrO: C,63.86%; H,9.31%. Found: C,63.66%; H,9.46%.

EXAMPLE 8

(Obtention of calcitriol)

To a suspension of Pd$_2$($^{dba}$)$_3$CHCL$_3$ (30 mg, 10% Pd) and triphenylphosphine (recrystallized from ethanol, 47 mg, 30%) is added freshly distilled toluene (2 mL) and triethylamine (3 mL). The mixture is vigorously stirred for about 10 minutes at room temperature. The solution of bromide of Example 7 (327 mg, 1.5 eq.) and enyne of Example 4 (299 mg, 0.61 mmol.) in toluene (1 mL) is added by gas tight syringe. The orange mixture is refluxed for 2 hours (oil bath at 125° C.) then cooled, and 5 mL of pentane are added. The resulting suspension is filtered over a small pad of silica, eluting with ethyl ether, and concentrated. Rapid chromatography of the yellow residue (ethyl ether/pentane, 2:1) affords 650 mg of a mixture of protected vitamin, protected previtamin, and bromide of Example 7, which is not separated by being subjected to desilylation by addition (under nitrogen and in the dark) of tetrabutylammonium fluoride (0.5M in THF, 6 mL, ca. 5 eq.). The resulting black solution is stirred for 30 hours at room temperature, then directly chromatographed (ethyl acetate) to afford 132 mg (52% from enyne of Example 4) of fairly pure calcitriol (Formula 6, X=OH) as a white solid.

The latter is recrystallized from chloroform to afford 103 mg of very pure calcitriol as white crystals.

Mp=109°-114° C. $[\alpha]_D^{25}$ +45.3 (c 0.44, ethanol). IR (neat): 1652, 1627, 1470, 1364, 1320, 1140, 1075, 1054, 915, 909 cm$^{-1}$. $^1$H NMR (400 MHz, acetone-d$_6$): 0.57 (s, 3H), 0.96 (d, 3H, J=6Hz), 1.06 (m, 1H), 1.13 (s, 6H), 1.21-2.10 (m, 19H), 2.27 (dd, 1H, J=7 and 13.5Hz), 2.49 (bd, J=13Hz), 2.74 (m, 1H, overlapped with the water peak at 2.80), 4.16 (m, 1H), 4.38 (m, 1H), 4.85 (bs, 1H), 5.31 (bs, 1H), 6.08 (d, 1H, J=12Hz), 6.28 (d, 1H, J=12Hz). $^{13}$C NMR (acetone-d6): 12.3, 19.2, 21.4, 23.0, 24.2, 28.3, 29.5, 36.9, 37.4, 41.3, 44.3, 45.3, 46.3, 46.4, 57.0, 57.4, 66.8, 70.0, 70.5, 110.8, 118.8, 123.9, 136.5, 141.3, 150.6.

EXAMPLE 9

(General Alkylative Enyne Cyclization Procedure)

A mixture of Pd$_2$(dba)$_3$CHCl$_3$ (2.6 mg, 0.005 mmol of Pd), triphenylphosphine (3.9 mg, .015 retool), and n-tetrabutylammonium halide (1.2 eq.) was dissolved in 1:1 solution of PhCH$_3$Pr$_2$NEt (0.5 mL each) and stirred at room temperature for 10 minutes, affording a yellow Pd(0) solution. The enyne (0.10 mmol) and the vinyl triflate (1.2 eq.) were added to the Pd solution and the reaction mixture heated as reflux until most of the starting materials were consumed as monitored by TLC. The reaction mixture was then cooled to room temperature, diluted with pentane (5 mL), filtered over Celite, the residue rinsed with Et$_2$O (5 mL), and the combined filtrates concentrated. The residue oil was then flash chromatographed on $SiO_2$ with a gradient of hexane to 5% EtOAc/hexane. This reaction then was repeated by making variations in ligand, halide source, reaction temperature, and reaction length, which are summarized in Table 2.

TABLE 2

| Ligand | Halide Source | Temp (°C.) | Time (h) | Isolated Yield |
|---|---|---|---|---|
| $PPh_3$ | LiBr | 100 | 21.5 | 28.3 |
| $PPh_3$ | LiBr | 100 | 21.5 | 44.5 |
| $PPh_3$ | $Bu_4NBr$ | 100 | 21.5 | 53.3 |
| $PPh_3$ | $Bu_4NCl$ | 100 | 21.5 | 47.3 |
| $PPh_3$ | $Bu_4NI$ | 100 | 21.5 | 44.5 |
| $PPh_3$ | $Oc_4NBr$ | 100 | 21.5 | 45.8 |
| $PPh_3$ | $Bu_4NI$ | 100 | 21.5 | 49.8 |
| $PPh_3$ | $Bu_4NI$ | 110 | 18.0 | 32.3 |
| $P(o\text{-anisyl})_3$ | $Bu_4NI$ | 110 | 7.0 | 41.3 |
| $P(p\text{-anisyl})_3$ | $Bu_4NI$ | 110 | 7.0 | 32.6 |
| $P(o\text{-anisyl})_3$ | $Bu_4NI$ | 100 | 4.0 | 34.1 |
| $P(o\text{-anisyl})_3$ | $Bu_4NBr$ | 100 | 4.0 | 46.3 |
| $P(o\text{-anisyl})_3$ | $Bu_4NBr$ | 100 | 4.0 | 48.4 |
| $PPh_3$ | $Bu_4NBr$ | 80 | 1.0 | 51.2 |
| $PPh_3$ | $Bu_4NBr$ | 80 | 1.0 | 49.8 |
| $PPh_3$ | $Ph_4PBr$ | 100 | 5.0 | 34.5 |
| $PPh_3$ | $Bu_4NBr$ | 100 | 3.0 | 50.8 |
| $PPh_3$ | $Bu_4NBr$ | 100 | 3.0 | 51.0 |
| $PPh_3$ | $Bu_4NBr$ | 100 | 3.0 | 49.0 |

In most instances (except with LiBr as halide source where $NEt_3$ was used as base) the base was $Ag_2CO_3$. The triflate was in a molar ratio with respect to halide source of 1:1.2.

It is to be understood that while the invention has been described above in conjunction with preferred specific embodiments, the description and examples are intended to illustrate and not limit the scope of the invention, which is defined by the scope of the appended claims.

It is claimed:

1. An alkylative cycloaddition method comprising:
   selecting a compound RX where X is a halide or a pseudo halide and R is a vinyl, an aryl or an alkyl lacking a β-hydrogen;
   providing a 1,6 enyne or a 1,7 enyne; and,
   reacting the selected compound RX with the enyne in the presence of a palladium catalyst to form a substituted bis(alkylidene)cycloalkane or a cyclohexadiene precursor as reaction product therefrom.

2. The method as in claim 1 wherein the reaction product formation includes generating a new carbon-carbon bond to cyclize the enyne while substantially stereospecifically introducing the aryl, vinyl or alkyl group of the selected compound.

3. The method as in claim 1 or 2 wherein the palladium catalyst is a palladium zero complex in its active state.

4. The method as in claim 3 wherein the palladium catalyst includes ligands and at least some of the ligands are trivalent phosphorous compounds.

5. The cycloaddition method as in claim 1 wherein the selected compound RX is an E-halomethylene or an E-pseudohalomethylene derivative of Grundmann's ketone wherein the pseudohalo substituent is capable of undergoing oxidative addition to a Pd(0) catalyst.

6. The cycloaddition method as in claim 1 wherein the selected compound RX is a substantially geometrically pure bromoolefin.

7. A compound useful in preparing Vitamin D analogues with a Vitamin D analogue side chain $R_1$, the compound having the structure

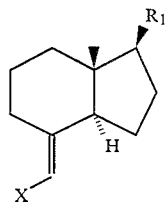

where X is a halide or a pseudo halide.

8. A method for the convergent synthesis of Vitamin D analogues having a Vitamin D analogue side chain $R_1$ and a Vitamin D analogue ring A comprising:
   providing a first precursor having the structure

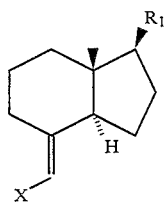

where X is a pseudo halide, and a second precursor, the second precursor being a 1,7 enyne; and,
   reacting the first and second precursors in the presence of a palladium catalyst and a source of halide ions to form a reaction product having a Vitamin D analogue ring A derived from the second precursor via a new carbon-carbon bond.

9. The method as in claim 8 wherein the palladium catalyst is a palladium zero complex in its active state.

10. The method as in claim 9 wherein the palladium catalyst includes ligands and at least some of the ligands are trivalent phosphorous compounds.

11. The method as in claim 10 wherein the ligands are phosphines or phosphites.

12. The method as in claim 8 wherein the enyne is 1-hexen-7-yn-3S,5R-diol or an ether thereof.

13. The method as in claim 8 wherein the reaction product has the structure

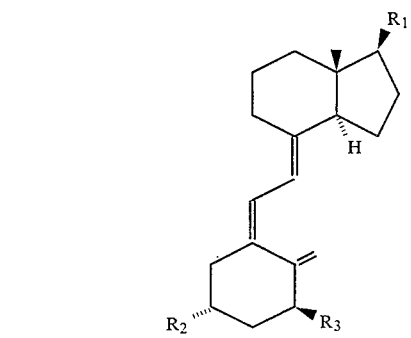

where $R_1$ is a Vitamin D analogue side chain, $R_2$ is hydrogen, hydroxyl, lower alkoxy, fluorine, or a protecting group, and $R_3$ is hydrogen, hydroxyl, lower alkoxy, fluorine, or a protecting group.

* * * * *

UNITED STATES PATENT AND TRADEMARK OFFICE
CERTIFICATE OF CORRECTION

PATENT NO. : 5,446,225
DATED : August 29, 1995
INVENTOR(S) : Trost et al.

Page 1 of 3

It is certified that error appears in the above-indentified patent and that said Letters Patent is hereby corrected as shown below:

In Column 4, line 59:
  replace "ide sources have been used (LiBr, Bu4NBr, Bu$_4$NCl," with:

--ide sources have been used (LiBr, Bu$_4$NBR, Bu$_4$NCL,--

In column 5, beginning at line 21:
  replace 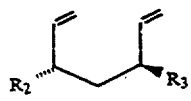 with: 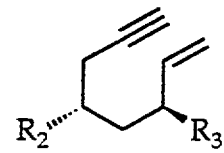

In column 7, beginning at line 23:
  replace 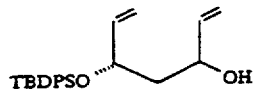 with: 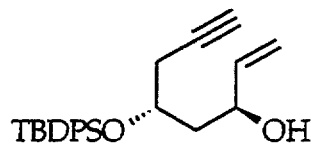

UNITED STATES PATENT AND TRADEMARK OFFICE
CERTIFICATE OF CORRECTION

PATENT NO. : 5,446,225
DATED : August 29, 1995
INVENTOR(S) : Trost et al.

It is certified that error appears in the above-indentified patent and that said Letters Patent is hereby corrected as shown below:

In Column 7, line 66:
    replace " To a stirred solution of alcohol (3R., 5R*) (190 mg,"
    with:

--   To a stirred solution of alcohol (3R*, 5R*) (190--

In Column 9, beginning at line 23:
    Replace:                              With:

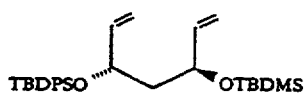      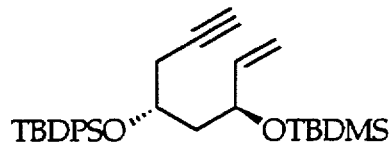

In Column 11, line 8:
    replace "yellow solid (79%, mP=131° C. pure by $^1$H NMR). A"
    with:

--yellow solid (79%, mp=131° C. pure by $^1$H NMR). A--

UNITED STATES PATENT AND TRADEMARK OFFICE
CERTIFICATE OF CORRECTION

PATENT NO. : 5,446,225
DATED : August 29, 1995
INVENTOR(S) : Trost et al.

It is certified that error appears in the above-indentified patent and that said Letters Patent is hereby corrected as shown below:

In Column 12, line 17:
Replace " To a suspension of $Pd_2(^{dba})_3CHCL_3$(30 mg, 10% Pd)" with:

-- To a suspension of $Pd_2(dba)_3CHCL_3$(30 mg, 10% Pd)--

In Column 12, line 60:
Replace "solution of $PhCH_3Pr_2NEt$ (0.5 mL each) and stirred at" with:

--solution of $PhCH_3-^iPr_2NEt$ (0.5 mL each) and stirred at--

Signed and Sealed this

Twentieth Day of February, 1996

Attest:

BRUCE LEHMAN

Attesting Officer    Commissioner of Patents and Trademarks